(12) United States Patent
List

(10) Patent No.: US 11,097,060 B2
(45) Date of Patent: Aug. 24, 2021

(54) INFUSION DEVICE DRIVE UNIT WITH BLOCKING DEVICE

(71) Applicant: Roche Diabetes Care, Inc., Indianapolis, IN (US)

(72) Inventor: Hans List, Oberzent (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 84 days.

(21) Appl. No.: 16/196,118

(22) Filed: Nov. 20, 2018

(65) Prior Publication Data
US 2019/0083712 A1 Mar. 21, 2019

Related U.S. Application Data

(63) Continuation of application No. PCT/EP2017/066585, filed on Jul. 4, 2017.

(30) Foreign Application Priority Data

Jul. 5, 2016 (EP) .................................... 16178003

(51) Int. Cl.
*A61M 5/315* (2006.01)
*A61M 5/145* (2006.01)
*A61M 5/24* (2006.01)

(52) U.S. Cl.
CPC ...... *A61M 5/31535* (2013.01); *A61M 5/1456* (2013.01); *A61M 5/14546* (2013.01);
(Continued)

(58) Field of Classification Search
CPC .......... A61M 5/14546; A61M 5/14566; A61M 5/1456; A61M 5/31511; A61M 5/31543;
(Continued)

(56) References Cited

U.S. PATENT DOCUMENTS 5,002,537 A * 3/1991 Hoffman ................. A61M 5/24
604/232
5,370,622 A * 12/1994 Livingston ............. A45C 11/22
224/247
(Continued)

FOREIGN PATENT DOCUMENTS

EP 1 484 071 A1 12/2004
EP 1 970 677 A1 9/2008
(Continued)

OTHER PUBLICATIONS

International Search Report and Written Opinion of the International Searching Authority, PCT/EP2017/066585, dated Sep. 29, 2017, 12 pages.

*Primary Examiner* — Bhisma Mehta
*Assistant Examiner* — James D Ponton
(74) *Attorney, Agent, or Firm* — Bose McKinney & Evans LLP

(57) ABSTRACT

Disclosed is an infusion device drive unit that includes a pump drive configured to operatively mechanically couple to a dosing unit to control operation of the dosing unit. The infusion device drive unit further includes a blocking member that is movable between a blocking configuration and a enabling configuration, the blocking member enabling the establishing and/or the releasing of an operative mechanical coupling between the pump drive and the dosing unit in the enabling configuration and preventing the establishing and/or the releasing of an operative mechanical coupling between the pump drive and the dosing unit in the blocking configuration. The infusion device drive unit controls the blocking member to take on the enabling configuration if the pump drive is in at least one pre-determined configuration and to take on the blocking configuration if the pump drive
(Continued)

is in a configuration different from a pre-determined configuration.

14 Claims, 2 Drawing Sheets

(52) U.S. Cl.
CPC .... *A61M 5/31511* (2013.01); *A61M 5/31543* (2013.01); *A61M 2005/2411* (2013.01); *A61M 2005/2433* (2013.01)

(58) Field of Classification Search
CPC .. A61M 2005/2411; A61M 2005/2433; A61M 2005/2437
See application file for complete search history.

(56) References Cited

U.S. PATENT DOCUMENTS

| | | | | |
|---|---|---|---|---|
| 5,788,673 | A | * | 8/1998 | Young ............... A61M 5/14526 604/131 |
| 5,954,697 | A | * | 9/1999 | Srisathapat ......... A61M 5/1456 604/154 |
| 2004/0249344 | A1 | * | 12/2004 | Nemoto .............. A61M 5/1458 604/151 |
| 2005/0256448 | A1 | * | 11/2005 | Angel ..................... F03G 7/065 604/68 |
| 2010/0049127 | A1 | | 2/2010 | Haueter et al. |
| 2011/0224644 | A1 | | 9/2011 | Haueter et al. |
| 2013/0261599 | A1 | | 10/2013 | Haueter et al. |
| 2013/0274696 | A1 | | 10/2013 | Lam |
| 2014/0039396 | A1 | | 2/2014 | Geipel et al. |
| 2014/0046288 | A1 | | 2/2014 | Geipel et al. |
| 2015/0057616 | A1 | | 2/2015 | Shergold et al. |
| 2015/0065958 | A1 | | 3/2015 | Teutsch et al. |

FOREIGN PATENT DOCUMENTS

| | | |
|---|---|---|
| EP | 2 653 180 A1 | 10/2013 |
| JP | 2005-287944 A | 10/2005 |
| RU | 2013 133 924 A | 1/2015 |
| WO | WO 2009/125398 A2 | 10/2009 |
| WO | WO 2013/010561 A1 | 1/2013 |

* cited by examiner

INFUSION DEVICE DRIVE UNIT WITH BLOCKING DEVICE

RELATED APPLICATIONS

This application claims priority to PCT/EP2017/066585, filed on Jul. 4, 2017, which claims priority to EP 16 178 003.6, filed on Jul. 5, 2016, the entire disclosures of which are hereby incorporated herein by reference.

BACKGROUND

The present disclosure lies in the field of infusion devices, in particular infusion device drive units. The disclosure lies further in the fields of ambulatory infusion devices, dosing units and methods for coupling a dosing unit with an infusion device drive unit.

Ambulatory infusion devices are well known in the art for the administration of liquid drugs, for example in the therapy of Diabetes Mellitus by Continuous Subcutaneous Insulin Infusion (CSII) as well as in pain therapy or cancer therapy. Ambulatory infusion devices are available from a number of suppliers, such as Roche Diabetes Care GmbH, Germany, or Medtronic MiniMed Inc., CA, USA.

According to a classic and well-established design, those ambulatory infusion devices or systems are typically of the syringe-driver type. The dosing precision of these systems largely relies on a well-defined coupling relation between the piston of the syringe-like drug cartridge and a plunger, which is part of the drive unit of the ambulatory infusion device. The well-defined coupling relation especially includes a well-defined relative position of the plunger rod and the piston.

When inserting a cartridge into the ambulatory infusion device, a coupling is well-defined if the relative position of the piston and the plunger rod, in particular a piston-coupling member of the plunger rod, is such that no piston displacement occurs upon coupling with the plunger rod. If, in contrast, the plunger rod is in a more advanced position as compared to the piston, the piston is pushed forward, resulting in an unintended drug delivery. If the plunger rod is in a more retracted position as compared to the piston, the piston may be retracted upon coupling, resulting in an undesired under pressure within the cartridge, and/or the coupling engagement may not be properly established, resulting in subsequent drive actuation not resulting in a corresponding piston displacement. Either of these scenarios is highly disadvantageous and may even result in serious medical complications in situations where the dosing unit or drug cartridge is fluidly coupled to a patient's body via an infusion cannula.

While the use of syringe-driver systems is well established, alternative system architectures have been recently proposed, for example in U.S. Publication No. 2010/049127 A1. While those alternative architectures show a number of advantages, the before-mentioned issue is also present for such systems and may even be more critical. For example, a system in accordance with the disclosure of U.S. Publication No. 2010/049127 A1 requires not only a well-defined piston displacement, but also a well-defined switching of a control valve. Further aspects and embodiments of such dosing units with a control valve are disclosed, e.g., in U.S. Publication No. 2010/049127 A1, U.S. Publication No. 2014/046288 A1, U.S. Publication No. 2014/039396 A1, U.S. Publication No. 2014/046288 A1, U.S. Publication No. 2013/261599 A1, U.S. Publication No. 2015/065958 A1, U.S. Publication No. 2015/057616 (A1), U.S. Publication No. 2011/224644 A1. Where the present disclosure makes reference to a dosing unit with a dosing cylinder and a control valve, the dosing unit may especially be designed in accordance with either one or a number of these prior art documents to which reference is accordingly specifically made and which are hereby incorporated by reference in their entireties.

SUMMARY

This disclosure teaches an improvement regarding the coupling and de-coupling of a drive unit and a dosing unit in the context of an ambulatory infusion system, which partly or fully eliminates the before-discussed problems.

The dosing unit is a functional and/or structural unit of an operational infusion system out of which liquid drug is dosed, i.e. dispensed, in well-defined, metered doses. The dosing unit may especially be a dosing unit that includes a miniaturized piston pump and a control valve that alternatively fluidly couples a dosing cylinder of the dosing unit with a drug inlet or outlet. Such dosing unit may, e.g. be designed in accordance with the disclosure of U.S. Publication No. 2010/049127 A1, to the disclosure of which reference is herewith made and which is hereby incorporated by reference in its entirety. Alternatively, the dosing unit may be realized or include a syringe-like drug cartridge with a cylindrical cartridge body and a sliding displaceable piston, the cartridge having a typical maximum filling volume in a range of 1 ml to 4 ml. This is the type of cartridge that is typically used in state-of-the art syringe driver systems as described before.

In an aspect, an infusion device drive unit is disclosed. Such infusion device drive unit typically forms an assembly group of an ambulatory infusion device. The infusion device drive unit includes a pump drive. The pump drive is configured to operatively mechanically couple to a dosing unit to control operation of the dosing unit.

The infusion device drive unit further includes a blocking device. The blocking device includes at least one blocking member. The blocking member is movable between a blocking configuration and an enabling configuration. The blocking member enables the establishing and/or the releasing of an operative mechanical coupling between the pump drive and the dosing unit in the enabling configuration. The blocking member prevents the establishing and/or the releasing of an operative mechanical coupling between the pump drive and the dosing unit in the blocking configuration.

The infusion device drive unit is further designed to control the blocking member to take on the enabling configuration if the pump drive is in at least one pre-determined configuration. The infusion device drive unit is further designed to control the blocking member to take on the blocking configuration if the pump drive is in a configuration different from a pre-determined configuration.

The blocking member comprises one or more structural elements that mechanically block or prevent an operative mechanical coupling between the pump drive and the dosing unit in the blocking configuration by way of mechanical interaction.

The at least one pre-determined configuration is a configuration of the drive unit where coupling and/or decoupling of piston driver and piston can be achieved in a controlled way. Favourably, a well-defined coupling without piston displacement as explained before can be established and/or released in such pre-determined configurations.

In some embodiments, the arrangement of the blocking device and its interaction with a dosing unit is further such that a dosing unit can only be inserted into or removed from a dosing unit compartment of an infusion device infusion device in the enabling configuration while insertion or removal from the dosing unit compartment is mechanically blocked by the blocking device in the blocking configuration.

In some embodiments, the pump drive includes a plunger rod. The plunger rod is displaceable along a displacement axis. The plunger rod is further designed to operatively mechanically couple with a piston of the dosing unit. In such embodiments, the operative mechanical coupling between the dosing unit and the pump drive that is enabled in the enabling configuration and is blocked in the blocking configuration is or includes a mechanical engagement of the plunger rod and the piston.

In some embodiments with a plunger rod, the pre-determined configuration is a configuration where the plunger rod is in a pre-determined position along its displacement axis. In some of those embodiments, a most retracted position of the plunger rod is a pre-determined position, preferably the only pre-determined position.

In some embodiments including a plunger rod, the plunger rod includes a control member. The control member interacts with the at least one blocking member. Thereby, the control member controls movement of the at least one blocking member between the blocking configuration and the enabling configuration. The configuration of the blocking member is accordingly determined by the position of the plunger rod along its displacement axis.

In some embodiments including a plunger rod, a travel range of the plunger rod along the displacement axis between a most retracted position and a most advanced position is 40 mm or less.

In some embodiments, the pump drive includes a valve controller. The valve controller is designed to operationally mechanically couple with a control valve of the dosing unit and to control a state of the control valve.

In some embodiments with a valve controller, the infusion device drive unit is designed to control movement of the at least one blocking member between the enabling configuration and the blocking configuration in dependence of a configuration of the valve controller.

In some embodiments, the at least one blocking member is arranged to move between the blocking configuration and the enabling configuration by a pivoting movement.

In some embodiments, the blocking device includes at least two blocking members. The at least two blocking members establish, in combination, a gripper structure, pincers structure and/or clamping structure.

In some embodiments, the blocking device includes at least one spring element. The at least one spring element is arranged to bias the at least one blocking member towards the blocking configuration.

In some embodiments, the at least one blocking member is arranged to clamp, in the blocking configuration, the dosing unit to maintain a predetermined operational position with respect to the infusion device drive unit.

In a further aspect, an ambulatory infusion device is provided. Favourably, the ambulatory infusion device is designed to be carried by a user for an extended time period and concealed from view. The ambulatory infusion device includes an infusion device drive unit, which may, for example, be an infusion device drive unit as described before and/or further below in the context of exemplary embodiments. Typically, the ambulatory infusion device further includes an electronic control unit, the electronic control unit being operatively electrically coupled to the pump drive, in particular an actuator of the pump drive. The electronic control unit is configured to control operation of the pump drive. It is noted, however, that the present disclosure may also be used in the context of systems without electronic control, for example, in systems with a mechanical spring drive as known in the art.

In some embodiments, the ambulatory infusion device is designed for the administration of a basal rate of liquid drug, favourably according to a time-varying basal administration schedule under control of the electronic control unit. The ambulatory infusion device may further be designed for the administration of liquid drug boli on demand upon a dedicated user command.

In a still further aspect, this disclosure teaches a dosing unit for use in combination with an infusion device drive unit and/or an ambulatory infusion device. The infusion device and/or the infusion device drive unit may, for example, be realized as described before and/or further below in the context of exemplary embodiments A dosing unit in accordance with the present disclosure further includes a blocking member engagement structure. The blocking member engagement structure is arranged to engage with the at least one blocking member in the blocking configuration and not to engage with the at least one blocking member in the enabling configuration.

According to a still further aspect, a method is disclosed for operatively coupling a dosing unit with an infusion device drive unit. The dosing unit and the infusion device drive unit may, for example, be as described before as well as further below in the context of exemplary embodiments. The method includes the steps of:
a) providing the infusion device drive unit with the at least one blocking member being in the blocking configuration;
b) controlling the pump drive to take on a pre-determined configuration;
c) moving the at least one blocking member from the blocking configuration into the blocking member releasing pre-determined configuration upon the pump drive taking on a pre-determined configuration.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

In this document, directional terms and phrases such as "left," "right," "above," "below," are generally used with reference to the figures and are only intended to support the reader's understanding. They do not imply any particular direction in operation.

Where relevant, the directions pointing in the direction of advancement and retraction, respectively, of the plunger rod are indicated by "A" and "R".

To improve clarity, elements that are present in several figures in the same or substantially the same way, are generally only referenced once.

It shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "blocking member," "pump drive," "dosing unit," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Figure 1A:
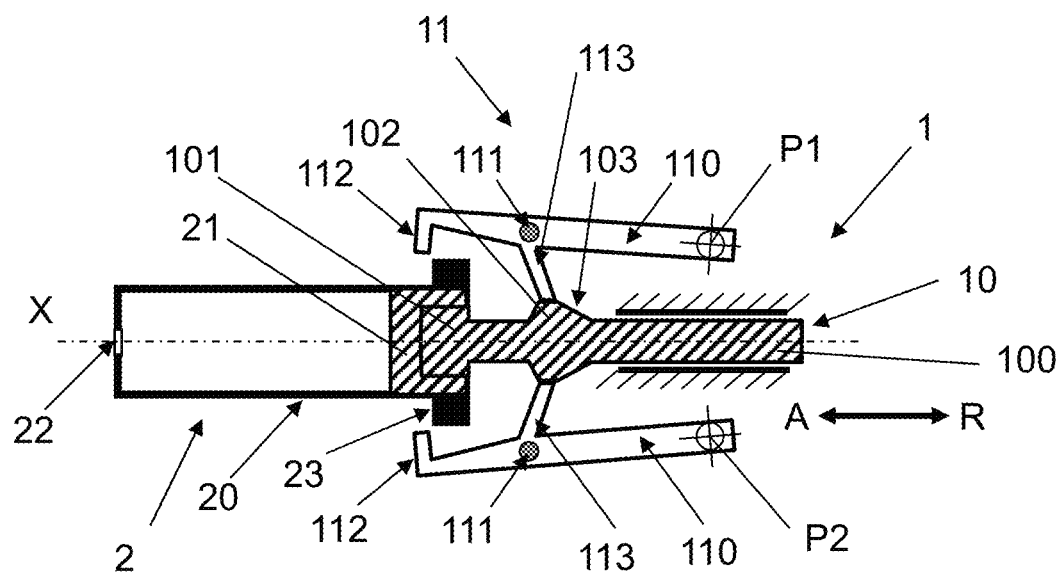
FIGS. 1a and 1b show a blocking device according to an exemplary embodiment together with associated elements in a blocking configuration and an enabling configuration respectively.
Figure 1B:
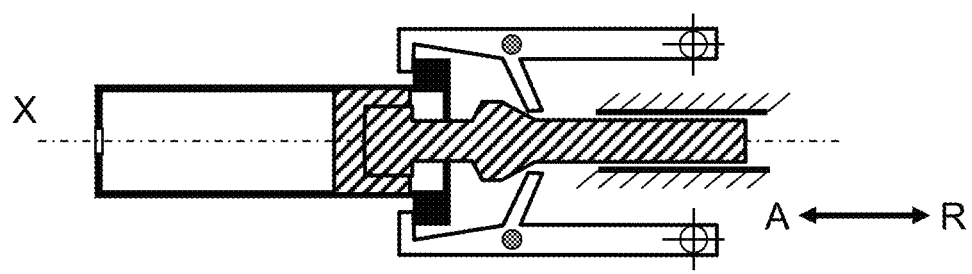

In the following, reference is first made to FIGS. 1a, 1b, showing part of an infusion device drive unit 1 together with part of a dosing unit 2 in two alternative configurations as discussed in the following.

Exemplarily, the dosing unit 2 includes a generally cylindrical dosing cylinder 20 with an open rear end. Inside the dosing cylinder 20, a piston 21 is sealingly and slidingly arranged along a longitudinal axis X. At the front end, the dosing cylinder 20 includes a fluidic aperture 22. By moving the piston into the advancement direction, liquid that is comprised inside the dosing cylinder 20 between the piston 21 and the front surface is expelled out of the dosing cylinder 20 through the fluidic aperture 22. Similarly, moving the piston 21 in the retraction direction results in liquid being drawn into the dosing cylinder 20 via the fluidic aperture 22.

In this embodiment, the fluidic aperture 22 is operatively fluidly coupled with a control valve (not shown) of the dosing unit 2 for alternatively and selectively fluidly coupling the fluidic aperture 22 with a liquid drug reservoir or an infusion line, respectively. The control valve is designed for operative mechanical and releasable coupling with a valve actuator and a valve actuation mechanism of the infusion device drive unit, e.g. via a rotary or linear displacement coupler, step switching mechanism, or the like. Alternatively, the control valve may be realized, in combination, by the dosing cylinder 20 and a stationary member (not shown) of the dosing unit 2, wherein the dosing cylinder 20 is movable, e.g. pivotable, with respect to the stationary member for the valve switching, as disclosed, e.g., in U.S. Publication No. 2011/0224644 A1, hereby incorporated by reference.

In still further embodiments, the dosing unit 2 does not include a control valve, but liquid drug is directly dispensed from the dosing cylinder 20 into an infusion line as it is the case for known syringe driver devices. The dosing cylinder 20 of such embodiments is realized as cartridge that stores a liquid drug amount for uninterrupted therapy, of typically a number of days, e.g. 1 ml-4 ml of liquid drug. The fluidic aperture 22 of such embodiments is fluidly coupled to or integral with an infusion line coupler, e.g. a known Luer coupler, or is directly connected with an infusion line and/or an infusion cannula.

At its rear end, the dosing cylinder 20 further includes a circumferential protrusion 23 in the form of a section of enlarged diameter. The protrusion 23 forms a blocking member engagement structure and is designed to interact with the blocking members of a blocking device as will be described further below.

Here and in the following, it is assumed that the dosing unit 2 is removably arranged in the dosing unit compartment (not shown) of an ambulatory infusion device. It is further assumed that the dosing unit 2 is secured inside the dosing unit compartment by walls of the dosing unit compartment, by stops, or the like, to maintain a well-defined and fixed position. The dosing unit 2 and the dosing unit compartment may further include corresponding mechanical engagement structures, such as catches, latches, a prismatic guide, or the like.

Furthermore, it is exemplarily assumed that the dosing unit 2 is inserted into the dosing unit compartment via an axial movement in the retraction direction and is removed from the dosing unit compartment via an axial movement into the advancement direction.

The exemplary infusion device drive unit 1 includes a plunger rod 10 that is part of a pump drive and is controlled to carry out a linear displacement movement between a most advanced position and most retracted position, respectively. FIG. 1a exemplarily shows the plunger rod 10 in the most retracted position. The plunger rod 10 is linearly guided, as schematically shown.

The pump drive further includes at least one actuator, typically in form of an electric motor, and optionally further intermediate components, in particular a reduction gear (not shown).

The plunger rod 10 includes an elongated plunger rod body 100 that is coaxial with and extends along the displacement axis X. At its front end, the plunger rod 10 further includes a piston coupler 101 for establishing a releasable operative mechanical coupling with the piston 21. This mechanical coupling between the piston coupler 101 and the plunger 21 is a push-pull coupling that allows a force transmission both in the advancement direction and the retraction direction, respectively. The piston 21 is accordingly moved in the advancement and retraction direction, respectively, by a corresponding displacement of the plunger rod 10. For such coupling, a number of designs are known in the art, for example a threaded coupling, a bayonet coupling, a magnetic or electromagnetic coupling, or a coupling via a brush- or pincher-like bracing structure of the piston coupler 101 that engages a corresponding cavity of the piston 21.

The plunger rod 10 further includes a circumferential control protrusion 102 that forms a control member and will be explained in more detail below.

The infusion device drive unit 1 further includes a blocking device 11 in accordance with the present disclosure. The blocking device 11 exemplarily includes two blocking members that are exemplarily realized as gripper arms 110. The gripper arms 110 are arranged radially spaced apart from and generally parallel to the plunger rod 10. At their front ends, the gripper arms 110 each comprise a gripper protrusion 112 that protrudes radially inwards. The gripper arms 110 are designed to interact and engage with the protrusion 23 of the dosing cylinder 20. The gripper arms 110 are pivotably arranged about corresponding pivoting axes P1, P2 close to their rear ends. The blocking device 11 further includes a spring element (also referred to herein as a "spring") that is exemplarily realized by a length of bent spring wire 111. The spring wire 111 engages corresponding bores of the gripper arms 110 and biases the gripper arms 110 radially inwards. The gripper arms 110 each further include a control cam 113 that points radially inwards towards the plunger rod 10 and is designed to interact and engage with the control protrusion 102.

In the following, operation of the exemplary blocking device 11 and associated components is explained in more detail. FIG. 1a shows the blocking device 11 in the enabling configuration and the plunger rod 10 in a pre-determined position. In the enabling configuration of FIG. 1a, a circumferential outer surface of the control protrusion 102 engages the control cams 113, thereby forcing the gripper arms 110 to pivot outwards, against an inwards-directed force that is exerted by the spring wire 111. In this configuration, the clearance between the gripper protrusions 112 is sufficient to enable an axial movement of the dosing unit 2. More specifically, the clearance between the gripper protrusions 112 is larger than the diameter of the protrusion 23.

In this specific example, the pre-determined position is a most retracted position and the only pre-determined position. This is a mechanically well-defined position by design. Likewise, a most retracted position of the piston 21 of the dosing unit 2 is well-defined. With the piston 21 and the plunger rod 10 both being in their respective most retracted positions, a mechanical coupling, for example a threaded coupling or a bayonet coupling, can be established or released between the piston coupler 101 and the piston 21 without displacement of the piston 21 within the dosing cylinder 20.

When, starting from the configuration shown in FIG. 1a, displacing the plunger rod 10 and the engaged piston 21 into the advancement direction, the inner ends of the control cams 113 will slide on the rear control surface 103 of the control protrusion 102. In accordance with the slope of the control surface 103, the gripper arms 110, will pivot inwards, driven by the biasing force that is exerted by the spring wire 111. The clearance between the gripper protrusions 112 decreases accordingly. At some point, the clearance between the gripper protrusions 112 becomes too small for the protrusion 23 of the dosing unit to pass between them.

FIG. 1b shows the situation where movement of the gripper arms 110 from the enabling configuration to the blocking configuration is complete. In this blocking configuration, the gripper arms 110 are swept inwards towards the plunger rod 10. The control cams 113 do not contact and engage the control protrusion 112 any longer. The protrusion 23 of the dosing unit 2 is axially arranged behind the gripper protrusions 112 and axial removal movement of the dosing unit 2 in the advancement direction is accordingly mechanically prevented.

When, starting from FIG. 1b, the plunger rod 10 and the coupled piston 21 are further advanced, the gripper arms 110 stay in the blocking configuration.

However, if the plunger rod 10 is again retracted, the above-explained steps will be carried out in the reverse direction, and the gripper arms 110 will accordingly pivot from the blocking configuration into the enabling configuration where the dosing unit 2 is free to be axially removed from the dosing unit compartment of the ambulatory infusion device.

The embodiment as shown in FIGS. 1a, 1b can be varied and/or modified in a number of ways. For example, it can be seen that the blocking configuration, and the transition between the blocking configuration and the enabling configuration, are defined by the axial position of the control protrusion 102 on the plunger rod body 100. By axially moving the control protrusion 102, any other desired position of the plunger rod 10 may be selected as pre-determined position.

By providing more than one control protrusion along the length of the plunger rod body 100, more than one pre-determined position may be foreseen. For example, the shown design may be modified such that both a most retracted axial rod plunger position and a most advanced axial plunger rod position is a pre-determined positions.

Furthermore, the number and specific arrangement of the gripper arms 110 may be modified. In the shown example of FIGS. 1a, 1b, two gripper arms 110 are present that are exemplarily arranged symmetrically and on diametrical sides of the plunger rod 10. Alternatively, only one gripper arm may be present or more than two gripper arms, for example three gripper arms at angles of 120°, may be present. Similarly, the blocking members may be arranged to selectively enable or prevent a movement of the dosing unit 2 in a direction different from the axial direction.

Alternatively to the spring wire 111, other types of spring elements may be used. For example, the spring wire 111 may be replaced by two discrete springs, each of them acting on one of the gripper arms 110. In further variants, no spring element is present but the blocking member(s), for example the gripper arms 110, are restraint guided in dependence of the axial position of the plunger rod 10.

In the following, reference is additionally made to FIGS. 2a, 2b, respectively, illustrating a further embodiment in accordance with the present disclosure.

Figure 2A:
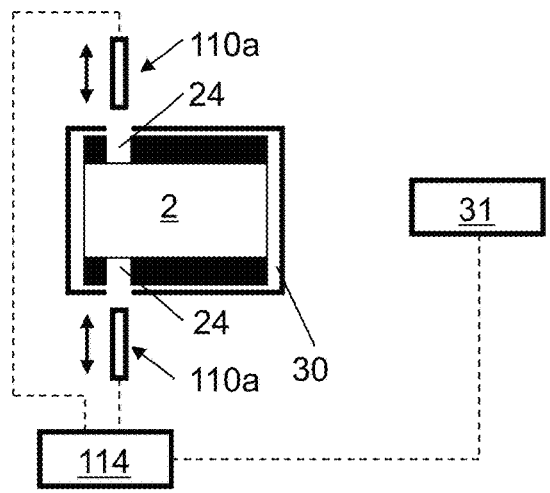
FIGS. 2a, 2b show a blocking device according to a further exemplary embodiment together with associated elements in a blocking configuration and an enabling configuration respectively.
Figure 2B:
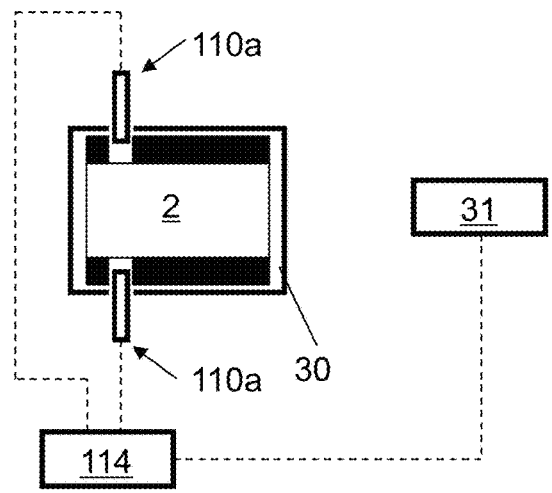

FIGS. 2a, 2b schematically show a dosing unit 2 arranged in the cartridge compartment 30 of an ambulatory infusion device. As blocking members, two blocking pins 110a are provided that are arranged displaceable along an axis as indicated by the corresponding arrows. In the blocking configuration (FIG. 2b), the blocking pins 110a engage corresponding recesses 24, a cut out, or the like of the dosing unit 2. In the enabling configuration (FIG. 2a), the blocking pins 110a do not engage the dosing unit 2. Unlike the previously discussed embodiment of FIGS. 1a, 1b, movement of the blocking pins 110a is not controlled mechanically via the plunger rod displacement. Instead, a dedicated blocking actuator 114, for example an electromagnetic actuator, is provided in operative mechanical coupling with the blocking pins 110a. The blocking actuator 114 is controlled from control circuitry 31 of the ambulatory infusion device.

Since the movement of the blocking pins 110a is electronically controlled in this example, any desired configuration of the pump drive may be selected as pre-determined configuration. For determining the plunger rod position, one or more position detecting device(s) like displacement encoder(s), position switch(es), etc. may optionally be provided. In the embodiment of FIGS. 1a, 1b, in contrast, the one or more enabling configurations is given by way of the mechanical design.

In the exemplary embodiments of FIGS. 1a, 1b, as well as FIGS. 2a, 2b, respectively, movement of blocking member between the blocking configuration and the enabling configuration is mainly discussed in dependence of a plunger rod position. If the ambulatory infusion device is designed for use in combination with a dosing unit having a control valve as discussed before, the generally same kinds of arrangement may be used for moving between the blocking configuration and the enabling configuration in dependence of a state of a valve actuation mechanism alternatively or additionally to the plunger rod position.

Figure 3:
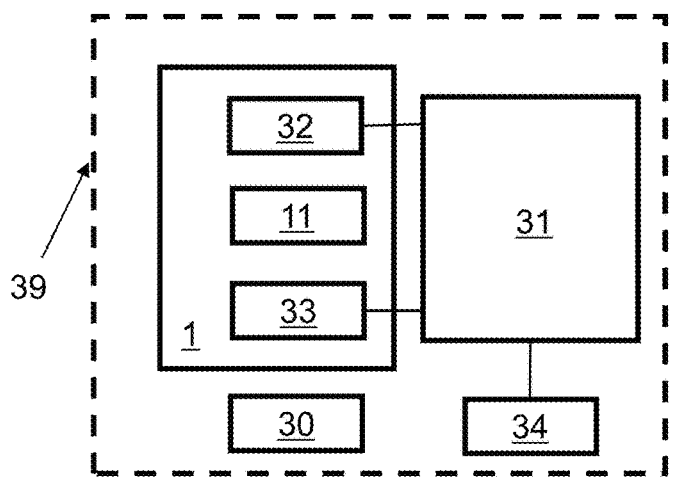
FIG. 3 shows an ambulatory infusion device in a schematic and functional view.

In the following, reference is additionally made to FIG. 3. FIG. 3 shows an ambulatory infusion device in a schematic functional view. The ambulatory infusion device may in particular be an ambulatory infusion device as mentioned above in the context of FIGS. 1a, 1b, and/or FIGS. 2a, 2b, and have structural and/or functional features as described.

The ambulatory infusion device comprises an electronics control unit or control circuitry 31 that may comprise one or more microcontrollers and/or microcomputers running corresponding firmware code, and/or further programmable components, such as ASICS, as well conventional active and/or passive circuitry. The electronic control unit 31 may further comprise a user interface and/or one or more communication interfaces.

The ambulatory infusion device further comprises an infusion device drive unit 1 that may be designed in accordance with any before-described embodiment. The infusion device drive unit 1 further includes a pump drive 32 that is controlled by the electronic control unit 31. The pump drive 32 includes an actuator such as motor like a standard DC motor, a brushless DC motor, or a stepper motor and may further include a reduction gear. The pump drive 32 further includes the plunger rod 10 which is controlled by the actuator to move as explained before in the context of FIGS. 1a, 1b and FIGS. 2a, 2b. Optionally, the infusion device drive unit 1 further includes a dedicated valve controller with a valve actuator 33 for switching a control valve of the dosing unit 2 as explained before. The infusion device drive unit 1 further includes a blocking device 11 according to any embodiment as mentioned before.

Optionally, the ambulatory infusion device includes one or more sensors 34. One or more sensors 34 may in particular be configured and arranged to detect a position, in particular a pre-determined plunger rod position of the plunger rod 10.

The ambulatory infusion device further includes at least one compartment 30 which may be a drug cartridge compartment and/or a dosing unit compartment.

The ambulatory infusion device further includes a housing 39 that is favourably designed to ensure a hermetically sealed and in particular water-protected or water-tight configuration in an operational state. The housing and the ambulatory infusion device as a whole are favourably shaped such that the ambulatory infusion device can be carried by a user over an extended time period of typically a number of days up to, e. g. a number of weeks, substantially continuously and concealed from view. Alternatively or additionally, the infusion device may be designed to be directly attached to a user's skin, in particular by way of an adhesive pad.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A drive unit for an infusion device, the drive unit comprising:
    a pump drive configured to couple to a dosing unit to control operation of the dosing unit, wherein the dosing unit has a dosing cylinder and a piston slidingly and sealingly arranged inside the dosing cylinder;
    a blocking member that is movable between a blocking configuration and an enabling configuration, wherein in the enabling configuration the blocking member permits coupling and decoupling of the pump drive and the dosing unit, and wherein in the blocking configuration, the blocking member prevents the coupling and decoupling of the pump drive and the dosing unit, wherein, in the blocking configuration, the blocking member is configured to engage the dosing cylinder; and
    a plunger rod that is displaceable along a displacement axis (X), the plunger rod configured to operatively couple with the piston of the dosing unit and wherein the movement of the blocking member between the blocking configuration and the enabling configuration is controlled by a position of the plunger rod along the displacement axis (X).

2. The drive unit according to claim 1, wherein when the plunger rod is in a most retracted position, the blocking member is in the enabling configuration.

3. The drive unit according to claim 1, wherein the plunger rod has a travel range along the displacement axis (X) between a most retracted position and a most advanced position of 40 mm or less.

4. The drive unit according to claim 1, further comprising a valve controller configured to operatively couple with the dosing unit.

5. The drive unit according to claim 1, wherein the blocking member is configured to move between the blocking configuration and the enabling configuration by a pivoting movement.

6. The drive unit according to claim 1, wherein the blocking member comprises at least two blocking members configured to work in combination to establish a gripper, pincers and/or clamps.

7. The drive unit according to claim 1, wherein the blocking member is configured to clamp, in the blocking configuration, the dosing unit to maintain a predetermined operational position.

8. An ambulatory infusion device configured to be carried by a user for an extended time period and concealed from view, the ambulatory infusion device comprising:
    a drive unit according to claim 1;
    an electronic control unit coupled to the pump drive and configured to control operation of the pump drive.

9. The ambulatory infusion device of claim 8, wherein the electronic control unit is coupled to an actuator of the pump drive.

10. A drive unit for an infusion device, the drive unit comprising:
    a pump drive configured to couple to a dosing unit to control operation of the dosing unit, wherein the dosing unit has a dosing cylinder and a piston slidingly and sealingly arranged inside the dosing cylinder;
    a blocking member that is movable between a blocking configuration and an enabling configuration, wherein in the enabling configuration the blocking member permits coupling and decoupling of the pump drive and the dosing unit, and wherein in the blocking configuration, the blocking member prevents the coupling and decoupling of the pump drive and the dosing unit, wherein, in the blocking configuration, the blocking member is configured to engage the dosing cylinder; and
    a plunger rod that is displaceable along a displacement axis (X), the plunger rod configured to operatively couple with the piston of the dosing unit and wherein the plunger rod includes a control member configured to interact with the blocking member to thereby control movement of the blocking member between the blocking configuration and the enabling configuration.

11. A drive unit for an infusion device, the drive unit comprising:
a pump drive configured to couple to a dosing unit to control operation of the dosing unit, wherein the dosing unit has a dosing cylinder and a piston slidingly and sealingly arranged inside the dosing cylinder;
a blocking member that is movable between a blocking configuration and an enabling configuration, wherein in the enabling configuration the blocking member permits coupling and decoupling of the pump drive and the dosing unit, and wherein in the blocking configuration, the blocking member prevents the coupling and decoupling of the pump drive and the dosing unit, wherein, in the blocking configuration, the blocking member is configured to engage the dosing cylinder; and
a valve controller configured to operatively couple with the dosing unit and wherein movement of the blocking member between the enabling configuration and the blocking configuration is controlled by the valve controller as a function of a configuration of the valve controller.

12. A drive unit for an infusion device, the drive unit comprising:
a pump drive configured to couple to a dosing unit to control operation of the dosing unit, wherein the dosing unit has a dosing cylinder and a piston slidingly and sealingly arranged inside the dosing cylinder;
a blocking member that is movable between a blocking configuration and an enabling configuration, wherein in the enabling configuration the blocking member permits coupling and decoupling of the pump drive and the dosing unit, and wherein in the blocking configuration, the blocking member prevents the coupling and decoupling of the pump drive and the dosing unit, wherein, in the blocking configuration, the blocking member is configured to engage the dosing cylinder;
wherein movement of the blocking member between the blocking configuration and the enabling configuration is determined by a position of the pump drive; and
a spring element configured to bias the blocking member towards the blocking configuration.

13. A system dosing unit in combination with an infusion device drive unit, comprising:
a dosing unit, comprising:
a dosing cylinder; and
a piston slidingly and sealingly arranged inside the dosing cylinder; and
an infusion device drive unit, comprising:
a pump drive configured to couple to the dosing cylinder to control operation of the dosing cylinder;
a blocking member that is movable between a blocking configuration and an enabling configuration, wherein in the enabling configuration the blocking member permits coupling and decoupling of the pump drive and the dosing cylinder, and wherein in the blocking configuration, the blocking member prevents the coupling and decoupling of the pump drive and the dosing cylinder and wherein, in the blocking configuration, the blocking member is configured to engage the dosing cylinder; and
a plunger rod that is displaceable along a displacement axis (X), the plunger rod configured to operatively couple with the piston of the dosing unit and wherein movement of the blocking member between the blocking configuration and the enabling configuration is controlled by a position of the plunger rod.

14. A method for operatively coupling the dosing unit and the infusion device drive unit of claim 13, the method comprising:
a) providing the infusion device drive unit with the blocking member in the blocking configuration;
b) controlling the pump drive of the infusion device drive unit to take on a pre-determined configuration; and
c) moving the blocking member from the blocking configuration into the enabling configuration upon the pump drive taking on the pre-determined configuration.

* * * * *

UNITED STATES PATENT AND TRADEMARK OFFICE
CERTIFICATE OF CORRECTION

PATENT NO. : 11,097,060 B2
APPLICATION NO. : 16/196118
DATED : August 24, 2021
INVENTOR(S) : Hans List Page 1 of 1

It is certified that error appears in the above-identified patent and that said Letters Patent is hereby corrected as shown below:

In the Claims

Column 12, Lines 3-4, Claim 13, the phrase "A system dosing unit in combination with an infusion device drive unit, comprising:" should read --A system, comprising:--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*